(12) United States Patent
Jaeger et al.

(10) Patent No.: US 10,016,574 B2
(45) Date of Patent: Jul. 10, 2018

(54) SYSTEM FOR PROVIDING BIOFEEDBACK

(75) Inventors: Mark Christoph Jaeger, Veldhoven (NL); Adrianus Johannes Maria Denissen, Moergestel (NL); Murray Fulton Gillies, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1190 days.

(21) Appl. No.: 13/991,633

(22) PCT Filed: Dec. 14, 2011

(86) PCT No.: PCT/IB2011/055664
§ 371 (c)(1),
(2), (4) Date: Mar. 21, 2014

(87) PCT Pub. No.: WO2012/080962
PCT Pub. Date: Jun. 21, 2012

(65) Prior Publication Data
US 2014/0249360 A1 Sep. 4, 2014

(30) Foreign Application Priority Data
Dec. 16, 2010 (EP) .................................... 10195284

(51) Int. Cl.
*A61M 21/02* (2006.01)
*A61B 5/0482* (2006.01)
*A61B 5/00* (2006.01)
*A61B 5/0484* (2006.01)
*A61B 5/048* (2006.01)
(Continued)

(52) U.S. Cl.
CPC ........... *A61M 21/02* (2013.01); *A61B 5/0482* (2013.01); *A61B 5/6844* (2013.01); *A61B 5/048* (2013.01); *A61B 5/04014* (2013.01); *A61B 5/04017* (2013.01); *A61B 5/04845* (2013.01); *A61B 5/165* (2013.01); *A61M 2021/0027* (2013.01)

(58) Field of Classification Search
None
See application file for complete search history.

(56) References Cited

U.S. PATENT DOCUMENTS 3,855,998 A 12/1974 Hidalgo-Briceno
4,184,485 A * 1/1980 Agoston ............ A61B 5/04845
128/905

(Continued)

FOREIGN PATENT DOCUMENTS

CN 1899639 A 1/2007
CN 101234224 A 8/2008
(Continued)

*Primary Examiner* — Charles A Marmor, II
*Assistant Examiner* — Shannon McBride

(57) ABSTRACT

The invention relates to a system (102) for providing biofeedback to a person (104). The system (102) comprises a source (106) for generating a source signal (108) and a transducer (110) for generating a measurement signal (112) in response to a physiological parameter (114) indicative for mental relaxation of the person (104). The system (102) furthermore comprises a filter (116) for variably filtering the source signal via modifying a cut-off frequency in response to the measurement signal (112) and an interface (118) for providing a biofeedback signal (119) to the person on the basis of the source signal as variably filtered by the filter (116).

13 Claims, 6 Drawing Sheets

Figure 1A:
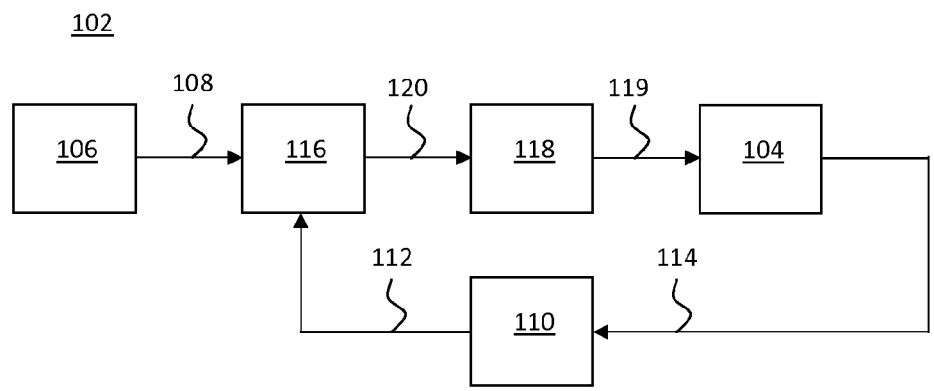

(51) Int. Cl.
    *A61B 5/04*     (2006.01)
    *A61B 5/16*     (2006.01)
    *A61M 21/00*    (2006.01)

(56)                References Cited

U.S. PATENT DOCUMENTS

| | | |
|---|---|---|
| 4,191,175 A | 3/1980 | Nagle |
| 4,275,744 A * | 6/1981 | Thornton ............. A61B 5/0484 |
| | | 600/544 |
| 4,334,545 A | 6/1982 | Shiga |
| 4,354,505 A | 10/1982 | Shiga |
| 4,883,067 A | 11/1989 | Snispel et al. |
| 6,623,427 B2 | 9/2003 | Mandigo |
| 2005/0177058 A1 * | 8/2005 | Sobell ................... A61B 5/0484 |
| | | 600/545 |
| 2007/0066403 A1 | 3/2007 | Conkwright |
| 2008/0177197 A1 | 7/2008 | Lee et al. |
| 2010/0060350 A1 * | 3/2010 | Zhang ................ H03H 11/1286 |
| | | 327/553 |

FOREIGN PATENT DOCUMENTS

| | | |
|---|---|---|
| EP | 0664683 | 9/1993 |
| GB | 1564631 A | 4/1980 |

\* cited by examiner

SYSTEM FOR PROVIDING BIOFEEDBACK

FIELD OF THE INVENTION

The invention relates to a system for providing biofeedback to a person.

BACKGROUND OF THE INVENTION

European patent EP 0664683 B1 discloses an electro encephalic neurofeedback apparatus. The apparatus comprises detecting means for detecting a bioelectric EEG signal including a set of bandwidths each having a range of one Hz around a selected frequency. The apparatus furthermore comprises sound means including respective music scores for each of said bandwidths. The sound means are configured for increasing said respective music scores in response to an increase in amplitude of said bandwidths as to increase the loudness of the music played to the patient.

Since the sound means raise the music's loudness in response to an increase of amplitude for some bandwidth, the patient is made well aware of the procedure to induce relaxation. Such awareness is not beneficial; in fact it is counterproductive as it may bring about additional stress. Therefore a problem of the apparatus is in its limited capability to effectively reduce a patient's stress level.

SUMMARY OF THE INVENTION

It is an object of the invention to provide a system for biofeedback capable of more effectively reducing a person's stress level. This object is achieved by the system according to the invention, which system comprises a source for generating a source signal, a transducer for generating a measurement signal in response to a physiological parameter indicative for mental relaxation of the person, a filter for variably filtering the source signal via modifying a cut-off frequency in response to the measurement signal, and an interface for providing a biofeedback signal to the person on the basis of the source signal as variably filtered by the filter.

By having a filter adapt a cut-off frequency to a measurement signal indicative for mental relaxation, and by subsequently filtering a source signal by such adaptive filter and by basing the biofeedback signal on such variably filtered source signal, the person is provided via the interface with biofeedback subtly adapted to changes in the person's state of mental relaxation. Therefore the system enables subconsciously inducing a relaxing effect thereby refraining from the person becoming aware of the system. Hence the person is not burdened with the feeling of being responsible for relaxing. Consequently the relaxing effect is not counteracted by stress that would be caused by such feeling. As a result the system according to the invention is capable of more effectively reducing a person's stress level.

The physiological parameter indicative for mental relaxation of the person e.g. a patient may be heart rate, heart rate variance, skin conductance, brain activity or a combination thereof.

The invention allows for application in the field health and well-being. For instance, persons having demanding jobs and experiencing significant stress as a result thereof may benefit from such application of the invention. Health and well being activities typically take place in a private setting e.g. at home hence not in a hospital environment. The invention furthermore allows for application in hospital settings i.e. instances in which the person is a patient, before and/or during medical procedures that induce significant stress levels to patients whereas the absence of such stress levels is instrumental for successfully completing the procedure. Examples of such medical procedures are Magnetic Resonance Imaging (MRI) and Positron Emission Tomography (PET) in conjunction with Computed Tomography (CT) imaging. During MRI examination patients are situated in a narrow bore of an MRI scanner among severe noise produced by said scanner. As a result patients experience considerable stress which negatively impacts imaging quality as it causes motion artifacts. Such stress is therefore to be reduced as much as possible. For the purpose of PET-CT imaging, a contrast agent comprising radioactively labeled sugar is intravenously administered to a patient. Since the uptake of said sugar by the human body is essentially non-specific, the tracer will gather at any location in the body where said sugar is consumed. Therefore the patient is required to remain as relaxed as possible during and after administering in order to minimize the amount of sugar consumed by the brain. Significant stress is however induced by the injection, by the confined geometry of the CT scanner in which the patient is to take place and by the fact that the patient is made aware that he should relax nonetheless. Therefore both MRI and PET-CT imaging may largely benefit from the system according to the invention.

In a preferred embodiment of the system according to the invention, the interface is arranged for generating a biofeedback signal comprising an audible component and the filter is configured for modifying its lowest cut-off frequency in response to the measurement signal. Hence, in this specific embodiment the source signal on which the biofeedback signal is based for example comprises information as contained at an optical storage disc or in files using a digital audio encoding format such as MP3. This embodiment realizes adaptively suppressing the lowest frequency content of an audible biofeedback signal i.e. the bass tones contained therein. Persons experience the low frequency content of such audible biofeedback as being closer when compared to the high frequency content. As a result this embodiment is capable of providing high impact biofeedback. Therefore this embodiment is advantageous in that it enables further reducing the person's stress level. The audible component may be a piece of music in order to make the biofeedback signal more enjoyable thereby advantageously increasing the effectiveness of biofeedback.

In a further preferred embodiment of the system according to the invention, wherein the transducer is arranged for generating the measurement signal in response to brain activity in a frequency range of 7 to 13 Hz. Hence, this embodiment is configured for providing neurofeedback. By selecting frequency contents in the range of 7 to 13 Hz, the transducer is capable of registering alpha brain activity, the level of which is known to correlate strongly with the person's level of mental relaxation. As a result this embodiment effectively addresses those parts of the brain associated with—or even responsible for—mental relaxation. Therefore this embodiment advantageously enables further reducing the person's stress level.

In a practical embodiment of the system according to the invention, the filter comprises a band-pass filter configured for modifying its lowest cut-off frequency in response to the measurement signal.

In a further practical embodiment of the system according to the invention, the filter comprises a high-pass filter configured for modifying its lowest cut-off frequency in response to the measurement signal.

In a further preferred embodiment of the system according to the invention, wherein the source is arranged for generating a biofeedback signal comprising an audible component, wherein the transducer is configured for generating the measurement signal in response to a physiological parameter which monotonically increases with mental relaxation of the person, wherein the system is arranged for computing a spectral power of the measurement signal and wherein the filter is arranged for modifying its lowest cut-off frequency in response to the spectral power according to a relation via which said lowest cut-off frequency monotonically decreases with said spectral power. In this text monotonically increasing implies non-decreasing whereas monotonically decreasing implies non-increasing. Brain activity in a frequency range of 7 to 13 Hz i.e. alpha brain activity and heart rate variance are examples of physiological parameters which monotonically increase with the person's level of mental relaxation. An increase in the level of spectral power associated with a measurement signal based on such brain activity thus indicates a more relaxed person. By increasingly amplifying the lower frequencies contained in the audible biofeedback signal via decreasing the filter's lowest cut-off frequency in response to a rise in the measurement signal's spectral power, this embodiment progressively rewards the person for achieving a higher level of relaxation. As a result, this embodiment is advantageous in that it enables more effectively reducing the person's stress level.

In a further preferred embodiment of the system according to the invention, wherein the source is arranged for generating a biofeedback signal comprising an audible component, wherein the transducer is configured for generating the measurement signal in response to a physiological parameter which monotonically decreases with mental relaxation of the person, wherein the system is arranged for computing a spectral power of the measurement signal and wherein the filter is arranged for modifying its lowest cut-off frequency in response to the spectral power according to a relation via which said lowest cut-off frequency monotonically increases with said spectral power. In this text monotonically increasing implies non-decreasing whereas monotonically decreasing implies non-increasing. Heart rate and skin conductance i.e. galvanic skin response are examples of physiological parameters that monotonically increase with to the person's level of mental relaxation. A decrease in the level of spectral power associated with such a measurement signal based on heart rate or skin conductance thus indicates a more relaxed person. By increasingly amplifying the lower frequencies contained in the audible biofeedback signal via decreasing the filter's lowest cut-off frequency in response to a decline of the measurement signal's spectral power, this embodiment progressively rewards the person for achieving a higher level of relaxation. As a result, this embodiment is advantageous in that it enables more effectively reducing the person's stress level.

In a further preferred embodiment of the system according to the invention, the filter is arranged for maintaining its cut-off frequency at a minimum frequency if the spectral power associated with the sample is smaller than a lower boundary of spectral power. By establishing such lower bound for the cut-off frequency, the extent to which the low-frequency content of the audible biofeedback signal is amplifiable by decreasing the filter's lowest cut-off frequency is limited. As a result, this embodiment effectively prevents exposing the person to an unnatural hence unpleasant biofeedback signal which may cause the person to become aware of the system for biofeedback. Consequently, as the person need not permanently and consciously try to relax, this embodiment has the advantage of more effectively reducing the person's stress level.

In a further practical embodiment of the system according to the invention, the minimum frequency is in the range of 0 Hz to 3 Hz.

In a further preferred embodiment of the system according to the invention, the filter is arranged for maintaining its lowest cut-off frequency at a maximum frequency if the spectral power associated with the sample is larger than the upper boundary of spectral power. By establishing such upper bound for the cut-off frequency, the extent to which the low-frequency content of the audible biofeedback signal is suppressible by increasing the filter's lowest cut-off frequency is limited. As a result, this embodiment effectively prevents exposing the person to an unnatural hence unpleasant biofeedback signal which may cause the person to become aware of the system for biofeedback. Consequently, this embodiment has the advantage of more effectively reducing the person's stress level.

In a further practical embodiment of the system according to the invention, the maximum frequency is in the range of 1500 Hz to 2500 Hz.

In a further preferred embodiment according to the invention, the system is arranged for generating a cumulative probability distribution on the basis of spectral power associated with the measurement signal, and wherein the system is arranged for computing the lower boundary and the upper boundary by equating the cumulative probability distribution to a lower level and an upper level, respectively. The nominal level of the spectral power associated with the measurement signal i.e. the level obtainable in the absence of stress is likely to vary from one person to another. Said nominal level may furthermore vary with time for a single person. By determining the lower and upper boundary on the basis of the actual measurement signal, this embodiment enables accounting for fluctuations in said nominal level. As a result this embodiment enables purposively modifying the lowest cut-off frequency by responding only to the stress induced portion of the measurement signal while passing over its nominal contents. Consequently, this embodiment advantageously more effectively reduces the person's stress level.

In a further preferred embodiment according to the invention, the interface comprises a pair of headphones in which the transducer is integrated. This embodiment integrates the interface and the transducer. As a result the amount of hardware that will potentially burden the person is effectively reduced. Consequently, this embodiment is advantageous in that it more effectively reduces the person's stress level. Alternatively, in a further preferred embodiment the interface may be integrated in a pillow which also accommodates the transducer.

The invention furthermore relates to a computer program product for use in the system according to the invention, comprising a computer readable medium having computer program code embodied therein which, when executed by a computer or a processor, is configured for causing the computer to embody a high-pass filter for variably filtering the biofeedback signal via modifying its cut-off frequency in response to the measurement signal.

The invention furthermore relates to a method for providing biofeedback to a person comprising the steps of generating a source signal, generating a measurement signal in response to a physiological parameter indicative for mental relaxation of the person, modifying a cut-off frequency of a frequency filter in response to the measurement signal, filtering the source signal by said pass filter, and providing the biofeedback signal to the person on the basis of the filtered source signal.

SHORT DESCRIPTION OF THE FIGURES

FIG. 1A schematically depicts an embodiment of the system according to the invention.

Figure 1B:
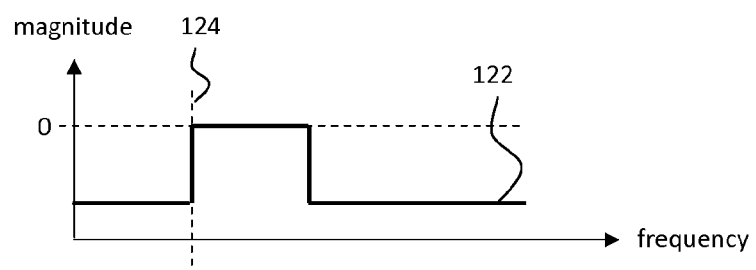
Figure 1C:
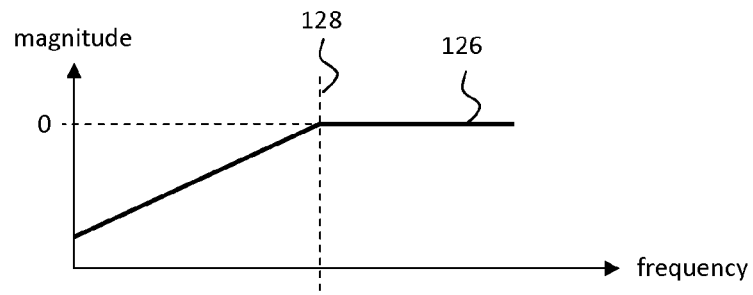

FIGS. 1B and 1C schematically depict a band-pass filter and a high-pass filter, respectively, for use in the embodiment depicted in FIG. 1A.

Figure 2A:
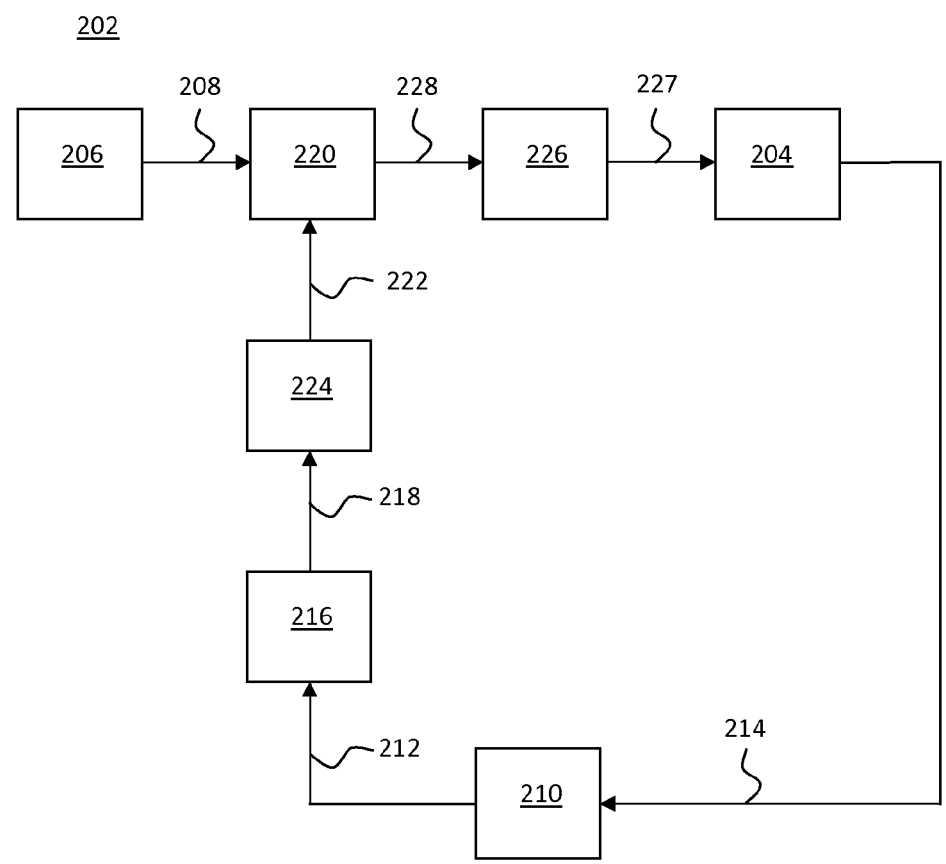

FIG. 2A schematically displays an embodiment of the system according to the invention wherein the system is arranged for computing a spectral power of the measurement signal and wherein the filter is arranged for modifying its lowest cut-off frequency in response to the spectral power.

FIGS. 2B, 2C, 2D and 2E provide graphical interpretation of algorithms for translating spectral power into cut-off frequency for use in the system displayed in FIG. 2A.

Figure 3A:
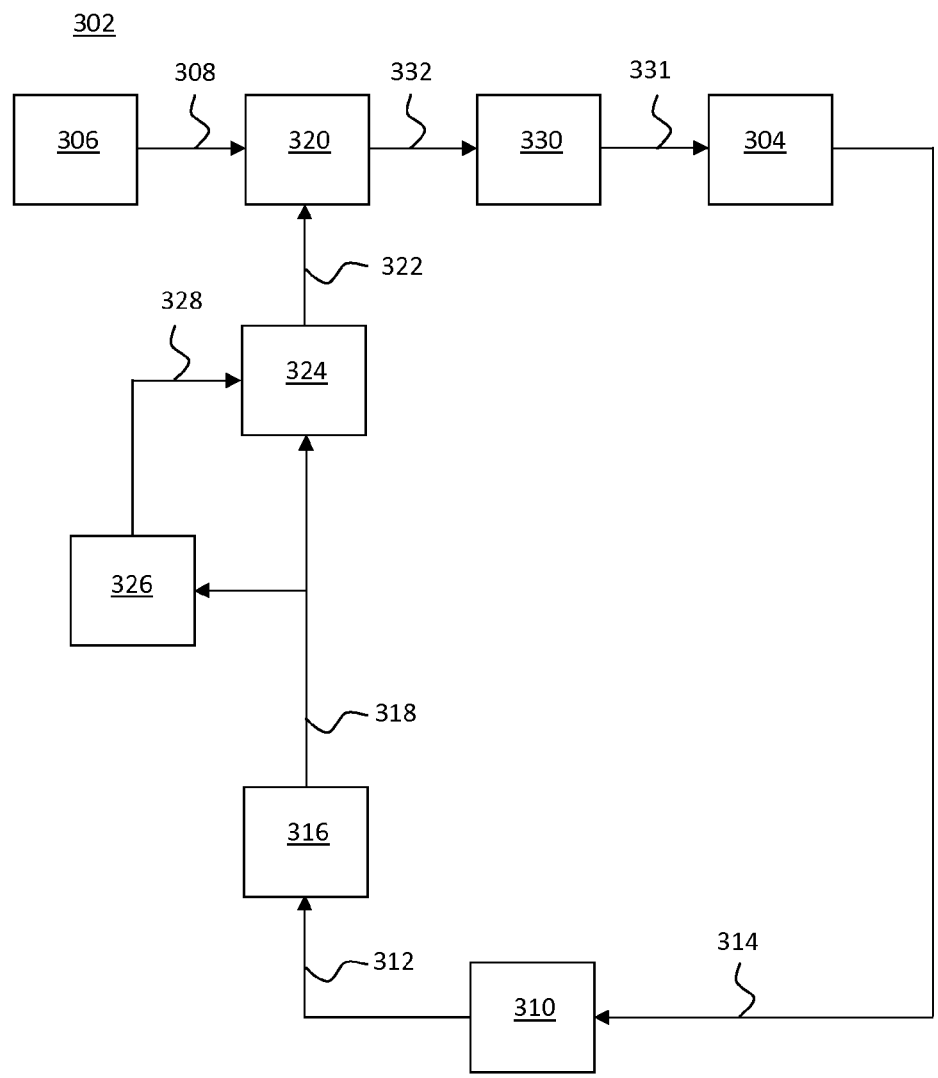

FIG. 3A schematically displays an embodiment of the system according to the invention wherein the system is arranged for generating a cumulative probability distribution of the spectral power of the measurement signal.

Figure 3B:
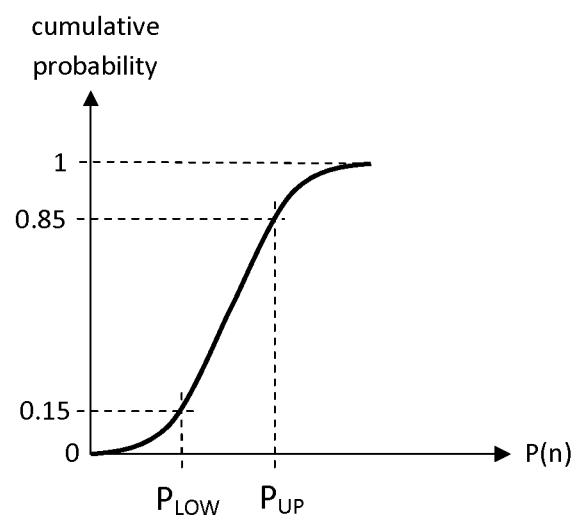
Figure 3C:
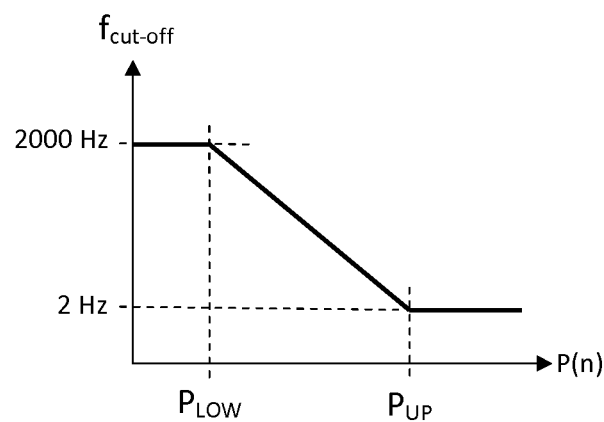

FIG. 3B and 3C provide graphical interpretation of algorithms for translating spectral power into cut-off frequency for use in the system displayed in FIG. 3A.

Figure 4:
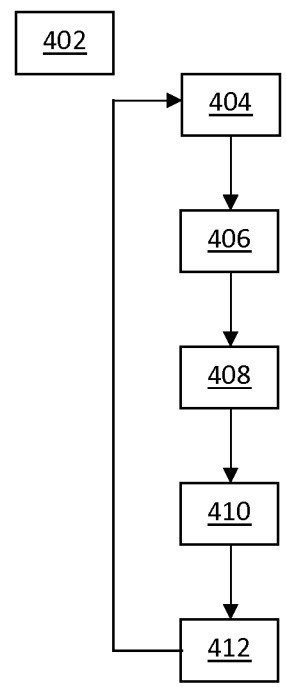

FIG. 4 schematically shows an embodiment of the method according to the invention.

DETAILED DESCRIPTION OF THE EMBODIMENTS

In the various figures, equal reference signs indicate similar features.

FIG. 1A displays a system 102 for providing biofeedback to a person 104 (including but not limited to a patient) comprising a source 106 for generating a source signal 108, a transducer 110 for generating a measurement signal 112 in response to a physiological parameter 114 indicative for mental relaxation of the person 104, a filter 116 for variably filtering the source signal 108 via modifying a cut-off frequency in response to the measurement signal 112, and an interface 118 for providing a biofeedback signal 119 to the person 104 on the basis of the source signal as variably filtered by the filter 116.

In a further example the transducer 110 comprises a non-invasive electrode to register brain activity and a processor for selecting frequency contents of such brain activity in the range of 6 to 14 Hz, preferably 7 to 13 Hz and more preferably 8 to 12 Hz, in response to which frequency contents the measurement signal is generated during use. Optionally the non-invasive electrode or the plurality thereof is integrated in a pair of headphones to be worn by the person.

FIG. 1B is a Bode plot depicting the magnitude of the frequency response function associated with a band-pass filter 122 which is optionally comprised in the filter 116. This Bode plot is depicted as a log-log graph i.e. employing logarithmic scales on both the horizontal and vertical axes. The band-pass filter 122 has a lower cut-off frequency 124 establishing the minimum frequency of a band in which frequencies are passed without modification i.e. without attenuation or amplification by the filter 116 during use. The band-pass filter 122 is configured for modifying its lower cut-off frequency 124 in response to the measurement signal 112. In terms of the Bode plot, said modification eventuates in horizontally shifting the lower cut-off frequency 124.

FIG. 1C is a Bode plot depicting the magnitude of the frequency response function associated with a high-pass filter 126 which is optionally comprised in the filter 116. This Bode plot is depicted as a log-log graph i.e. employing logarithmic scales on both the horizontal and vertical axes. The high-pass filter 126 has a cut-off frequency 128. Frequencies below the cut-off frequency 128 are being suppressed by the high-pass filter 126 during operational conditions whereas frequencies above the cut-off frequency 128 are being passed without modification. The high-pass filter 126 is configured for modifying its cut-off frequency 128 in response to the measurement signal 112. In terms of the Bode plot, said modification eventuates in horizontally shifting the cut-off frequency 128. The high-pass filter 126 may be provided with first-order dynamics, but may equally well be of higher order.

FIG. 2A displays a system 202 for providing biofeedback to a person 204 (including but not limited to a patient) comprising a source 206 for generating a source signal 208 and a transducer 210 which in this specific example is arranged for generating a measurement signal 212 in response to a physiological parameter 214 that monotonically increases with mental relaxation of the person 204. Examples of physiological parameters having such quality include but are not limited to alpha brain activity. In this particular example, system 202 comprises a processor 216 arranged for computing a spectral power 218 of the measurement signal 212. System 202 furthermore comprises a filter 220 arranged for modifying its lowest cut-off frequency 222 in response to the spectral power 218 according to a relation via which said lowest cut-off frequency 222 monotonically decreases with said spectral power 218. In this specific case, said relation is embedded in a processor 224 known per se. System 202 furthermore comprises an interface 226 for providing the person 204 with an audible biofeedback signal 227 on the basis of the source signal 208 as variably filtered by the filter 220. The audible biofeedback signal 227 may comprise a piece of music. The interface 226 utilizes technologies known per se such as a pair of headphones. Preferably, the transducer 210 is integrated in said pair of headphones.

Figure 2B:
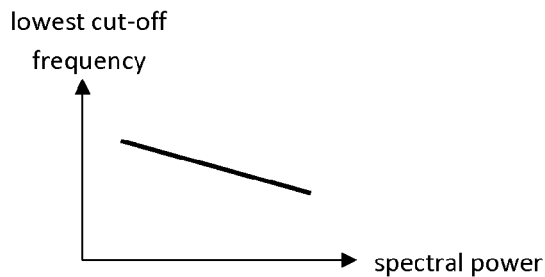
Figure 2C:
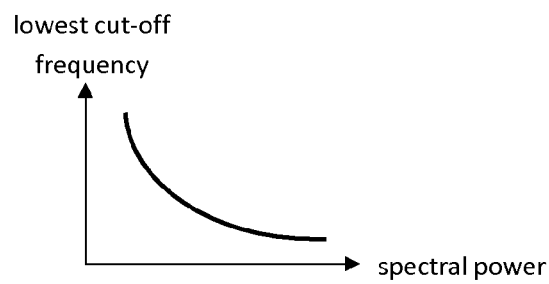

FIGS. 2B and 2C depict examples of the relation mapping the spectral power 218 of the measurement signal 212 onto the lowest cut-off frequency 222 of the filter 220. The relations depicted in FIGS. 2B and 2C respectively establish monotonically decreasing linear and exponential mappings between spectral power 218 and cut-off frequency 222. The exponential mapping shown in FIG. 2C has a monotonically decreasing first derivative with respect to spectral power 218. Consequently, such exponential mapping is advantageous in that it progressively rewards higher levels of spectral power 218 i.e. higher states of relaxation.

Alternatively, in a different example, the transducer 210 is arranged for generating a measurement signal 212 in response to a physiological parameter that monotonically decreases with mental relaxation of the person 204. Examples of physiological parameters having such quality include but are not limited to heart rate and skin conductance i.e. galvanic skin response. In cooperation therewith, referring to FIG. 2A, the processor 224 defines a relation via which the lowest cut-off frequency 222 monotonically decreases with the spectral power 218.

Figure 2D:
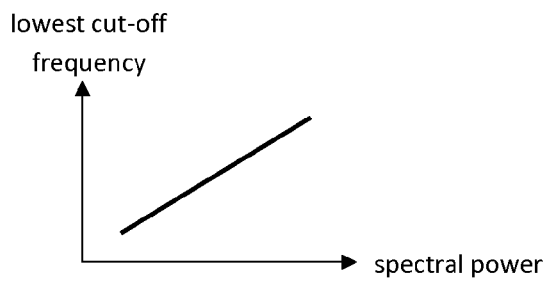
Figure 2E:
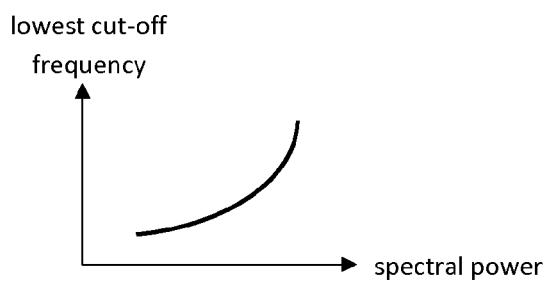

FIGS. 2C and 2D depict examples of the relation mapping the spectral power 218 of the measurement signal 212 onto the lowest cut-off frequency 222 suitable for use in system 202 provided the transducer 210 is arranged for measuring a physiological parameter that monotonically decreases with the person's level of relaxation. The relations depicted in FIGS. 2B and 2C, respectively, establish monotonically increasing linear and exponential mappings between spectral power 218 and cut-off frequency 222.

FIG. 3A displays a system 302 for providing biofeedback, more specifically neurofeedback, to a person 304 (including but not limited to a patient). The system 302 comprises a source 306 for generating a source signal 308 and a transducer 310 which in this specific example is arranged for generating a measurement signal 312 in response to alpha brain activity 314. In this particular example, system 302 comprises a processor 316 arranged for computing a spectral power 318 of a sample n of the measurement signal 312. System 302 furthermore comprises a filter 320 arranged for modifying its lowest cut-off frequency 322 in response to spectral power 318 according to the following relation:

$$f_{cut-off}(P(n)) = \begin{cases} f_{cut-off,max} & \text{for } P(n) < P_{LOW} \\ \frac{f_{cut-off,max} - f_{cut-off,min}}{P_{UP} - P_{LOW}}(P_{LOW} - P(n)) + f_{cut-off,min} & \text{for } P_{LOW} \le P(n) \le P_{UP} \\ f_{cut-off,min} & \text{for } P(n) > P_{UP} \end{cases}$$

wherein P denotes spectral power, wherein n denotes the $n^{th}$ sample of the measurement signal 312 and wherein $f_{cut-off}$ (P(n)) denotes the cut-off frequency in response to the spectral power associated with said $n^{th}$ sample.

Via this relation $f_{cut-off}$ monotonically and linearly decreases with said spectral power P(n) if P(n) has a value in between a lower boundary $P_{LOW}$ and an upper boundary $P_{UP}$. If spectral power P(n) is smaller than $P_{LOW}$, the filter 320 maintains its cut-off frequency $f_{cut-off}$ at a maximum level denoted by $f_{cut-off,max}$. If spectral power P(n) exceeds $P_{UP}$, the filter 320 will maintain its cut-off frequency at a minimum level defined by $f_{cut-off,min}$. The maximum level is in the range of 1500 Hz to 2500 Hz whereas said minimum level is in the range of 1 Hz to 3 Hz. In this specific example, $f_{cut-off,max}$=2000 Hz and $f_{cut-off,min}$=2 Hz. FIG. 3B provides a graphical interpretation of the relation for mapping spectral power P(n) onto cut-off frequency $f_{cut-off}$.

Referring to FIG. 3A, said relation is implemented via processor 324. In this particular example system 302 furthermore comprises a processor 326, known per se, configured for generating a cumulative probability distribution 328 on the basis of spectral power 318 associated with samples of the measurement signal 312. The processor 326 is furthermore arranged for computing the lower boundary $P_{LOW}$ and the upper boundary $P_{UP}$ by equating the cumulative probability distribution to a lower level and an upper level, respectively. For example, the lower level is set at 0.15 whereas the higher level is set at 0.85. FIG. 3C provides a graphical interpretation of the cumulative probability distribution 328.

Referring to FIG. 3A once more, system 302 comprises an interface 330 for providing the person or person 304 with a neurofeedback signal 331. Said neurofeedback signal 331 comprises an audible component such as a piece of music and is generated on the basis of the source signal 308 as variably filtered by the filter 320. For providing the person or person 304 with the neurofeedback signal 331, the interface 330 employs technologies known per se such as a pair of headphones.

FIG. 4 schematically displays a method 402 for providing biofeedback to a person comprising the steps of generating 404 a biofeedback signal, generating 406 a measurement signal in response to a physiological parameter indicative for mental relaxation of the person, modifying 408 a cut-off frequency of a frequency filter in response to the measurement signal, filtering 410 the biofeedback signal by said pass filter, and providing 412 the biofeedback signal to the person.

While the invention has been illustrated and described in detail in the drawings and in the foregoing description, the illustrations and the description are to be considered illustrative or exemplary and not restrictive. The invention is not limited to the disclosed embodiments. Other combinations of embodiments are feasible. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system for providing biofeedback to a person comprising:
    a source configured to generate a source signal,
    a transducer configured to generate a measurement signal in response to a physiological parameter indicative of mental relaxation of the person,
    a processor for computing a spectral power of the measurement signal,
    a filter configured to variably filter the source signal via modifying a lowest cut-off frequency in response to the spectral power, and
    an interface configured to provide a biofeedback signal to the person based on the source signal as variably filtered by the filter in response to the spectral power.

2. The system according to claim 1 wherein the interface is arranged to provide a biofeedback signal comprising an audible component.

3. The system according to claim 2, wherein the transducer is configured for generating the measurement signal in response to a physiological parameter which monotonically increases with mental relaxation of the person, wherein the filter is arranged for modifying the lowest cut-off frequency in response to the spectral power according to a relation via which said lowest cut-off frequency monotonically decreases with said spectral power.

4. The system according to claim 3, wherein the filter is arranged for maintaining the cut-off frequency at a minimum frequency if the spectral power is smaller than a lower boundary of spectral power.

5. The system according to claim 4, wherein the minimum frequency is in a range of 0 Hz to 3 Hz.

6. The system according to claim 3, wherein the filter is arranged for maintaining the lowest cut-off frequency at a maximum frequency if the spectral power is larger than an upper boundary of spectral power.

7. The system according to claim 6, wherein the maximum frequency is in a range of 1500 Hz to 2500 Hz.

8. The system according to claim 3, wherein the system is arranged for generating a cumulative probability distribution on a basis of the spectral power associated with samples of the measurement signal, and wherein the system is arranged for computing a lower boundary of spectral power and an upper boundary of spectral power by equating the cumulative probability distribution to a lower level and an upper level, respectively.

9. The system according to claim 2, wherein the transducer is configured for generating the measurement signal in response to a physiological parameter which monotonically decreases with mental relaxation of the person, wherein the filter is arranged for modifying the lowest cut-off frequency in response to the spectral power according to a relation via which said lowest cut-off frequency monotonically increases with said spectral power.

10. The system according to claim 1, wherein the transducer is arranged to generate the measurement signal in response to brain activity in a frequency range of 7 to 13 Hz.

11. The system according to claim 1, wherein the interface comprises a pair of headphones in which the transducer is integrated.

12. A computer program product for use in the system according to claim 1, comprising a non-transitory computer readable medium having computer program code embodied therein which, when executed by a computer or a processor, is configured for causing the computer or processor to embody a filter for variably filtering the biofeedback signal via modifying the lowest cut-off frequency in response to the spectral power.

13. A method for providing biofeedback to a person comprising the steps of:
generating a source signal via a source,
generating a measurement signal via a transducer in response to a physiological parameter indicative of mental relaxation of the person,
computing a spectral power of the measurement signal via a processor,
modifying a lowest cut-off frequency of a frequency filter automatically in response to the spectral power,
filtering the source signal by said frequency filter, and
providing a biofeedback signal to the person via an interface, based on the filtered source signal.

* * * * *